United States Patent [19]

Senior et al.

[11] Patent Number: 4,902,717
[45] Date of Patent: Feb. 20, 1990

[54] PROSTAGLANDINS

[75] Inventors: Judith Senior, Otley; Kay M. Troughton, Skipton, both of England

[73] Assignee: National Research Development Corporation, London, England

[21] Appl. No.: 913,672

[22] PCT Filed: Jan. 16, 1986

[86] PCT No.: PCT/GB86/00028
§ 371 Date: Sep. 3, 1986
§ 102(e) Date: Sep. 3, 1986

[87] PCT Pub. No.: WO86/04234
PCT Pub. Date: Jul. 31, 1986

[30] Foreign Application Priority Data

Jan. 16, 1985 [GB] United Kingdom ................ 8501035

[51] Int. Cl.$^4$ .................. A61K 31/34; A61K 31/557; A61K 31/175
[52] U.S. Cl. .................................. 514/562; 514/461; 514/530; 514/532; 514/583
[58] Field of Search ............... 514/562, 530, 532, 469, 514/583

[56] References Cited

U.S. PATENT DOCUMENTS

| | | | |
|---|---|---|---|
| 4,418,076 | 11/1983 | Nakane et al. | 514/562 |
| 4,430,345 | 2/1984 | Jones et al. | 514/562 |
| 4,438,136 | 3/1984 | JOnes et al. | 514/562 |
| 4,456,615 | 6/1984 | Nakane et al. | 514/562 |
| 4,536,510 | 8/1985 | Wasserman et al. | 514/562 |
| 4,596,823 | 6/1986 | Jones | 514/529 |
| 4,628,061 | 12/1986 | Jones et al. | 514/562 |

FOREIGN PATENT DOCUMENTS

| | | | |
|---|---|---|---|
| 0013608 | 7/1980 | European Pat. Off. . | |
| 0043292 | 1/1982 | European Pat. Off. . | |
| 94792 | 11/1983 | European Pat. Off. | 514/530 |
| 107995 | 5/1984 | European Pat. Off. | 514/530 |
| 0111955 | 6/1984 | European Pat. Off. . | |
| 2039430A | 8/1980 | United Kingdom | 514/567 |
| 2039909A | 8/1980 | United Kingdom | 514/562 |
| 2081258A | 4/1982 | United Kingdom | 514/562 |
| 2092589A | 8/1982 | United Kingdom | 514/562 |
| 2113678A | 8/1983 | United Kingdom | 514/562 |
| 2119375A | 11/1983 | United Kingdom | 514/567 |

OTHER PUBLICATIONS

Honn, Clin Exp. Metastasis 1983, vol. 1, No. 2, pp. 103–114.
K. V. Honn et al., "Thromboxanes and Prostacyclin . . . " Biochem. & Biophy. Research Comm. vol. 102, No. 4, Oct. 30, 1981.
K. V. Honn et al., "Thromboxane Synthetase . . . " J. Cell Biol., vol. 87, nr. 2II, 1980, p. 64, entry No. CI442.
O. Ylikorkala et al., "Prostacylin & Thromboxane . . . " Gynecologic Oncology, vol. 16, Academic Press, Inc. 1983, pp. 340–345, entire doc.
D. L. McCormick et al., "Inhibitio of Mammary . . . " Br.J. Cancer, vol. 48, 1983, pp. 859–861.
K. V. Honn, "Inhibition of Tumor Cell . . . " Clin. Exp. Metastasis, vol. 1, No. 2, 1983, pp. 103–114.
J. K. Clayton et al., "The Effects of Prostaglandins . . . " Br. J. Pharmacol. vol. 78, Mar. 1983, p. 53P.
J. Senior et al.; "Modification of Uterine . . . " Br. J. Pharmacol, vol. 81, Mar. 1984, p. 73P.
D. J. Weatherall et al. (editors) "Medical Aspects of Neoplasia" Oxford Textbook of Medicine, vol. 1, Sects. 1–12, pp. 4.87–4.97.
C. W. Parker et al., "Formation of Thromboxane . . . " the Jour. of Immunology, vol. 122, No. 4, Apr. 1979, pp. 1572–1577.
F. Fitzpatrick et al., "9,11-Iminoepoxyprosta-5, 13-Dienoic . . . " Bio. et Biophysica Acta, 573 (1979) pp. 238–244.
M. Verstraete "Introduction: Thromboxane in . . . " Br. J. Clin. Pharmac. (1983) 15, pp. 7S–11S.
K. V. Honn et al., "Control of Tumor Growth and . . . " Interaction of Platelets & Tumor Cells N.Y. 1982, pp. 295–331.
J. K. Clayton et al., "A Comparison of Responses . . . " 6th Intl. Conf. on Pros. Jun 1986 Florence (Italy) Abstracts p. 107.
J. K. Clayton et al., "Prostanoid Receptors in the . . . " 6th Intl. Conf. on Pros. Jun. 1986 Florence (Italy) Abstracts p. 107.
J. K. Clayton et al., "The Effects of Prostaglandins . . . " Br. J. Pharmac. (1983) 78, p. 53P.
M. Nakane et al., "Aza-Substituted . . . " Advances in Pros. Throm. & Leu. Res., vol. 15, Raven Press, N.Y. 1985, pp. 291–293.
The Merck Index tenth Edition Merck & Co., Inc. U.S.A. 1983, pp. 1300,830,499 and 65.

Primary Examiner—Robert Gerstl
Attorney, Agent, or Firm—Nixon & Vanderhye

[57] ABSTRACT

Compounds having thromboxane antagonist activity are of use in the treatment of hormone-dependent neoplasias for example oestrogen-dependent neoplasias. Thromboxane antagonists of particular value are compounds of formula (I)

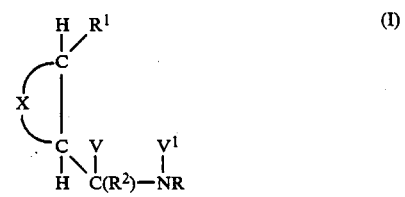

wherein

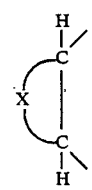

(Abstract continued on next page.)

represents one of the divalent cyclic groups

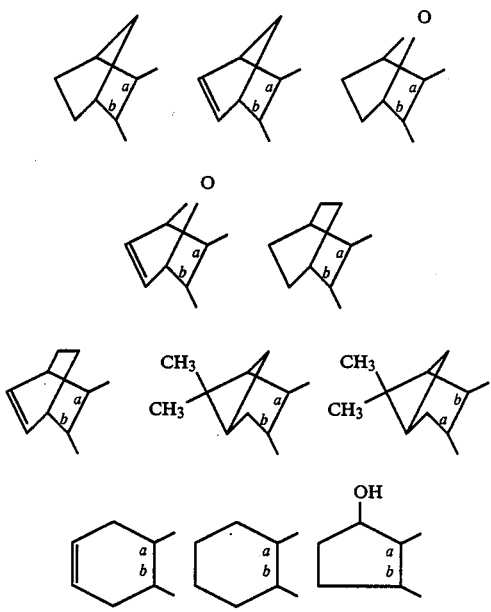

the letters a and b indicating in each case the points of attachment of the substituents $R^1$ and $CV(R^2)$—$NV'R$, respectively; $R^1$ is a 6-carboxyhex-2-enyl group or a modification thereof in which the group is altered by one, or an appropriate combination of two or more, of the following: (a) alteration of the position of the double bond, (b) reduction of the double bond, (c) alteration of the chain length through a decrease of one or two methylene groups or an increase of one to six methylene groups, (d) replacement of one or two methylene groups each separately by an oxygen or sulphur atom with the proviso that in the modified group no oxygen or sulphur atom is in an alpha position relative to either a doubly bonded carbon atom or to the carboxy group or a derivative thereof and that at least 2 carbon atoms separate any pair of oxygen and/or sulphur atoms; and (e) formation of an amide, ester or salt derivative of the carboxy group; V and V' either each separately is hydrogen or together are the second bond of a carbon-nitrogen double bond; $R^2$ is hydrogen, an aliphatic hydrocarbon group or an aliphatic hydrocarbon group substituted by an aromatic group directly or through an oxygen or sulphur atom; and R is a group —NH.CO.NH—$R^3$ or —NH.CS.NH—$R^3$ wherein $R^3$ is an aliphatic hydrocarbon group, an aromatic group or an aliphatic hydrocarbon group substituted by one or more aromatic groups directly or through an oxygen or sulphur atom.

21 Claims, No Drawings

PROSTAGLANDINS

This invention relates to the treatment of neoplastic and in particular of hormone-dependent neoplasias.

Certain neoplasias, for example prostatic, mammary and endometrial carcinomas, are hormone-dependent and such neoplasias may be treated not only with cytotoxic agents but also by altering the hormonal status of the patient. However, although such endocrine therapy can produce worthwhile results, there is the same urgent need in this area as exists with other types of neoplastic disease for improvement in the existing methods of treatment.

We have now found that compounds possessing thromboxane antagonist activity have a previously quite unexpected use in the treatment of hormone-dependent neoplastic disease, this being an area quite unconnected with the existing pharmaceutical uses for such compounds. One group of compounds described as having activity at thromboxane receptor sites which is of particular interest in the context of the present invention comprises those compounds developed by Jones and Wilson and described in UK patent Nos. (a) 2039909, (b) 2039480; (c) 2081258 and (d) 2113678 and their equivalents [(a) European Pat. No. 0013607, Japanese Pat. application No. 80/500131 and U.S. Pat. No. 4,430,345; (b) European Pat. 0013,608, Japanese Pat. application No. 80/500132 and U.S. Pat. No. 4,438,136; (c) European Pat. application No. 81303000.4, Japanese Pat. application No. 81/502230 and U.S. patent application No. 349,084; and (d) European Pat. application 82306605.5, Japanese Pat. application 83/500327 and U.S. patent application 531,899].

In addition to the description of the medical uses of these compounds to be found these patent specifications, reports upon certain of the compounds have appeared in the scientific literature concerning investigations of a more academic character into the detailed nature of their activity, but without identifying any further uses for the compounds beyond those described in the patent specifications. The present invention is based upon an appreciation that one facet of the activity of these and other compounds having thromboxane antagonist activity provides a further valuable medical use for them.

Accordingly the present invention comprises a compound having thromboxane antagonist activity for use in the manufacture of a medicament for use in the treatment hormone-dependent neoplasias.

The present invention is based upon an appreciation that it is possible to utilise the newly discovered additional properties possessed by compounds having thromboxane antagonist activity of inhibition of the growth of hormone-dependent, particularly oestrogen-dependent, tissue and stimulation of blood flow to such tissue in the treatment of neoplastic disease. Thus the compounds may be applied to the treatment of neoplastic disease in hormone-dependent tissue either alone or in conjunction with hormonal therapy agents and/or with cytotoxic agents when the effect produced by these agents can be enhanced. The use of the compound alone to produce an inhibitory effect on the growth of the neoplastic tissue is clearly of value per se and by using the compound together with a hormonal therapy agent the effect upon growth produced by the compound augments that produced by the agent. When the compound is used in conjunction with a cytotoxic agent the effect of the compound will be to selectively improve the blood flow through the neoplastic tissue and thereby increase the selectivity of the cytotoxic agent.

Thromboxane antagonist compounds of use in the present invention may be of various types. The compounds of particular interest are those which are inhibitors acting at the thromboxane $A_2$ ($TXA_2$) receptor site. These may take a wide variety of forms, extending to thromboxane antagonists described by other workers as well as those described in the four UK patents referred to hereinbefore. The antagonists include non-prostanoid compounds such as 4-[2-benzenesulphonamido-ethyl]-phenoxyactic acid, and N,N'-bis-[7-(3-chlorobenzeneaminosulphonyl)-1,2,3,4-tetrahydroisoquinolyl]-disulphonylimide and related compounds described in U.S. Pat. No. 4,536,510.

Of greater interest, however, are the prostanoid compounds which generally contain an abnormal $\omega$-chain and may also contain an $\alpha$-chain and/or ring system which is modified from that present in the naturally occurring prostaglandins. Even within this group of compounds there is wide diversity of structures. One group of compounds consists of the aza derivatives which are exemplified by 13-azaprostanoic acid and related compounds which are described in in U.S. Pat. No. 4,239,778, and 9,11-dimethylmethano-11,12-methano-16-phenyl-13,14-dihydro-13-aza-15$\alpha\beta$-$\omega$-tetranor-TXA$_2$, 9,11-dimethylmethano-11,12-methano-16-(4hydroxphenyl)-13,14-dihydro-13-aza-15$\alpha\beta$-$\omega$-tetranor-TXA$_2$, 9,11-dimethylmethano-11,12-methano-16-(4-methoxyphenyl)-13,14-dihydro-13-aza-15$\alpha\beta$-$\omega$-tetranor-TXA$_2$, 9,11-dimethylmethano-11,12-methano-16-(3-iodo-4-hydroxyphyenyl)13,14-dihydro-13-aza-15$\alpha\beta$-$\omega$-tetranor-TXA$_2$ and 9,11-dimethylmethano11,12-methano-15-phenyl-13,14-dihydro-13-aza-15$\alpha\beta$-$\omega$ pentanor-TXA$_2$ and related compounds which are described in European Pat. No. 0044711. A further group of compounds based upon a 1,3-dioxan ring system which is exemplified by the compound 5(Z)-7-(2,2-dimethyl-4-phenyl-1,3-dioxan-cis-5-yl)-heptenoic acid and also comprises the related compounds described in European Pat. applications 0145260, 0142324 and especially 0094239, especially those compounds, in the free acid or ester form, which correspond to this named compound but with a substituted rather and an unsubstituted phenyl group and particularly with a modification of the 5(Z)-heptenoic acid chain, or which are isomers of the named compound, for example the compound 5(Z)-7-(2,2-dimethyl-5-phenyl-1,3-dioxan-trans-4-yl)heptenoic acid. Further variations containing a cyclohexane rather than a 1,3-dioxan ring system are described in European Pat. application 0142322. Another group of compounds of some particular interest is based upon an oxygen substituted cyclopentane or cyclopentene ring system and is exemplified by the compounds [1$\alpha$(Z), 2$\beta$, 5$\alpha$]-methyl-7-[2-(4-morpholinyl)-3-oxo-5-(phenylmethoxy)cyclopentyl]-5-heptenoate and especially [1$\alpha$(Z), 2$\beta$, 5$\alpha$]-7-[5-([(1,1-biphenyl)-4-yl]methoxy]-2-(4-morpholinyl)-3-oxocyclopentyl]-4-heptenoic acid, and also comprises the related compounds described in UK Pat. Nos. 2075503, 2070591 and especially 2028805 (the later patent being equivalent to U.S. Pat. Nos. 4,265,891, 4,409,213 and 4,447,428), particularly those compounds, in the free acid or ester form, which correspond to the two specifically named compounds but with a different grouping at the 5-position, or which are isomers of the named compound.

Among the prostanoid type of thromboxane antagonists those containing a bridged ring system are some particular interest including various compounds containing the 7-oxabicyclo [2,2,1] heptane ring system, for example [1 α2β(5Z), 3β(1E), 4α]-7-[3-(3-cyclohexyl-3-hydroxy-1-propenyl)-7-oxabicyclo [2,2,1]hept-2-yl]-5-heptenoic acid. Other such compounds are those described in UK Pat. application No. 2119375 (equivalent to U.S. Pat. No. 4,418,076), European Pat. application No. 0107995 (equivalent to U.S. Pat. No. 4,456,615) and especially European Pat. application No. 0094792 (equivalent to U.S. Pat. 4416896), particularly those compounds, in the free acid or ester form, which correspond to this named compound but with a modification of the 5(Z)-heptenoic acid chain and/or which are isomers of the named compound. Such compounds containing the 7-oxabicyclo [2,2,1] heptane ring system and representing modifications of the Jones and Wilson compounds are described further hereinafter in relation to the compounds of formulae (I) and (II).

Among the many thromboxane antagonists described in the patent and scientific literature, certain of the compounds described in UK Pat. Nos. 2039480 and 2081258, together with modifications of these compounds, represent a selected sub-group of thromboxane antagonists which is of particular interest for use in the present invention. This sub-group comprises compounds of formula (I)

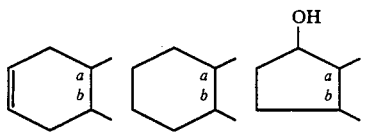
(I)

wherein

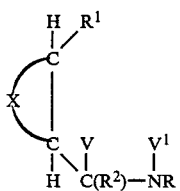

represents one of the divalent cyclic groups

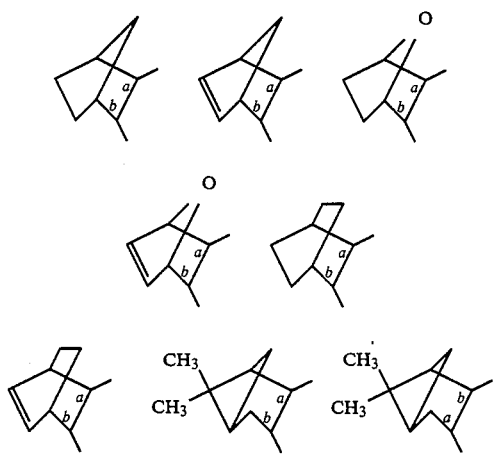

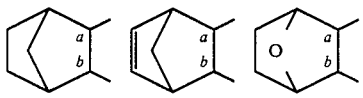

the letters a and b indicating in each case the points of attachment of the substituents $R^1$ and $CV(R^2)$—$NV'R$, respectively; $R^1$ is a 6-carboxyhex-2-enyl group or a modification thereof in which the group is altered by one, or an appropriate combination of two or more, of the following: (a) alteration of the position of the double bond, (b) reduction of the double bond, (c) alteration of the chain length through a decrease of one or two methylene groups or an increase of one to six methylene groups, (d) replacement of one or two methylene groups each separately by an oxygen or sulphur atom with the proviso that in the modified group no oxygen or sulphur atom is in an alpha position relative to either a doubly bonded carbon atom or to the carboxy group or a derivative thereof and that at least 2 carbon atoms separate any pair of oxygen and/or sulphur atoms; and (e) formation of an amide, ester or salt derivative of the carboxy group; V and V' either each separately is hydrogen or together are the second bond of a carbon-nitrogen double bond; $R^2$ is hydrogen, an aliphatic hydrocarbon group or an aliphatic hydrocarbon group substituted by an aromatic group directly or through an oxygen or sulphur atom; and R is a group —NH.CO.NH—$R^3$ or —NH.CS.NH—$R^3$ wherein $R^3$ is an aliphatic hydrocarbon group, an aromatic group or an aliphatic hydrocarbon group substituted by one or more aromatic groups directly or through an oxygen or sulphur atom.

The various bridged ring systems indicated above may alternatively be represented in planar form, i.e. in the same order as

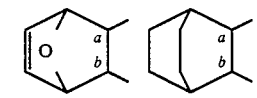

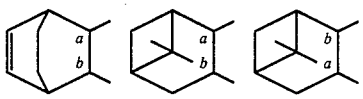

(the two free valancies in the centre of the last two formulae indicating methyl groups), but the more usual convention has generally been followed throughout the specification of representing these systems in non-planar form. It will be appreciated, however, that various stereoisomeric forms of the compounds (I) may be used in the invention. In particular, different geometric isomers can exist and most of these will occur in two enantiomorphic forms. For the bridged ring compounds (I) these two forms will have the structure illustrated hereinbefore and the mirror image of that structure. Taking the vicinally disubstituted bicyclo [2,2,1] heptane ring system as an example, such pairs of enantiomorphs may be shown as follows (the rings being numbered according to the system used herein).

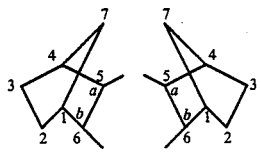

For the sake of added clarity it might be mentioned that alternative, equivalent, modes of showing these non-planar structures may be used. Thus the right hand of the two formulae shown directly above is equivalent to

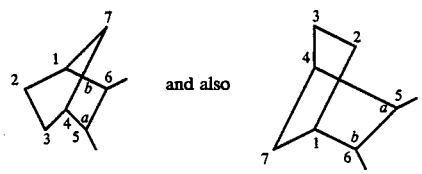

It will be seen that the modifications of the 6-carboxyhex-2-enyl group which may be made in compounds (I) used in the present invention are of two types. Thus, the modifications either involve the hex-2-enyl group or the 6-carboxy group. Among modifications of the first form, which are listed under (a) to (d) above, certain preferences may be indicated. Thus, if the position of the double bond is altered from the 2,3-position this is more usually to the 5,6-position or more particularly the 4,5-position and especially the 3,4-position. Where the hex-2-enyl group is modified, however, compounds in which the double bond is reduced are of particular interest. Modifications of types (c) and (d) are therefore more often effected together with a modification of type (b). Where the chain length is decreased, this is more often by one methylene group only and where it is increased, this is more often by one to four or particularly one or two methylene groups, an increase in chain length being of generally greater interest than a decrease. A chain of 5 or especially 6 to 8 atoms terminally substituted by a carboxy group or a derivative thereof is therefore generally preferred. When no oxygen or sulphur atom is present a chain of 6 atoms is preferred but in chains containing an oxygen or sulphur atom the position is slightly different as described hereinafter.

The proviso given above under modification (d) precludes the replacement of the methylene group adjacent to the carboxy group but one, or less often two, methylene groups at any of the other Positions 1 to 5 can each be replaced either by oxygen or sulphur subject to the requirement that those methylene groups are not adjacent to a doubly bonded carbon atom and necessarily that the position is not occupied by a double bond. Replacement at positions 2 and 3, in conjunction with reduction of the double bond present in the unmodified group, is of some particular interest and, indeed, the replacement of a methylene group at any position is more often effected in conjunction with the reduction of the double bond. Also worth particular mention, however, is replacement of the methylene group at the 5-position. As is also the case with alteration of the double bond to the 4,5-position, such a modification is of especial interest when no modification of type (c) is also made which involves the end of the carbon chain adjacent to the carboxy group. Thus, groups $R^1$ of some interest containing oxygen and/or sulphur are those of the form $-(CH_2)_b-(A)_a-(CH_2)_c-B-CH_2-CO_2H$ and amide, ester and salt derivatives thereof, in which A and B are each separately oxygen or sulphur and either a is 0, b is 0 and c is an integer from 2 to 10, or a is 1, b is 0 or an integer from 1 to 7 and c is an integer from 2 to 9 with the sum of b and c being from 2 to 9. Variations in the group $R^1$ can involve the $-(CH_2)_b-(A)_a-(CH_2)_c-B-CH_2$chain or the terminal $-C_2R'$ group. It is preferred that a is 0 and that B is oxygen. However, when a is 1, A and B are conveniently each sulphur or, more especially, oxygen. Chains of a total of between 4 and 8 or 10 atoms terminally substituted by a carboxy group or a derivative thereof are of most interest with a preference for chains of at least 5 or particularly 6 or more atoms. Compounds containing a chain of 7 atoms have quite unexpectedly shown some improvement in properties as compared with those containing a chain of 6 atoms, this being the chain length of the 6-carboxyhex-2-enyl group occurring in natural prostaglandins. When a is 0, therefore, c is preferably 3, 4, 5, 6 or 7, particularly 4, 5 or 6. When a is 1, b+c is preferably 2, 3, 4, 5 or 6 particularly 3, 4 or 5 and it is also preferred that b is greater than 0 and that c is 2 or 3, the compounds in which a is 1 which are of particular interest being those in which c is 2 and b is 1,2 or 3, and those in which c is 3 and b is 0 or especially 1 or 2.

It will be appreciated from the foregoing that a group of compounds (I) of same especial interest consists of compounds in which $R^1$ is a 6-carboxyhex-2-enyl group or a modification thereof in which the group is altered by one, or an appropriate combination of two or more, of the following: (a) alteration of the position of the double bond, (b) reduction of the double bond, (c) alteration of the chain length through a decrease or an increase of one or two methylene groups, (d) replacement of a methylene group by an oxygen or sulphur atom with the proviso that in the modified group the oxygen or sulphur atom is not in an alpha position relative to either a doubly bonded carbon atom or the carboxy group or a derivative thereof, and (e) formation of an amide, ester or salt derivative of the carboxy group.

As regards the second type of modification of form (e) listed above, the carboxy group derivatives may be (i) esters, especially alkyl esters, for example those containing a $C_1-C_{10}$ alkyl group but particularly methyl or ethyl esters; (ii) amides, which may contain a group $-CONH_2$ or such a group in which the nitrogen atom is substituted, especially by one or two groups selected from substituted or unsubstituted phenyl groups, for example as described hereinafter, alkyl groups, for example $C_1-C_{10}$ alkyl groups, and from more complex groups such as $-SO_2CH_3$ or an analogue thereof containing a $C_2-C_{10}$ alkyl group, for example to provide a group of the form $-CONHSO_2CH_3$; and (iii) salts with various physiologically acceptable cations. Salt derivatives are of especial interest, specific examples of salts being those formed with an alkali metal such as sodium or with quaternary ammonium ions or amines such as tris (the symbol tris represents the compound 2-amino-2-hydroxymethylpropane 13-diol). It will be appreciated that many of such compounds containing a modification of form (e) are in fact bioprecursors for the corresponding compound containing a carboxy group to which they are converted in vivo.

Examples of specific groups $R_1$ are —$(CH_2)_2O(CH_2)_3CO_2H$, —$(CH_2)_4OCH_2CO_2H$, —$(CH_2)_5OCH_2CO_2H$, —$(CH_2)_6OCH_2CO_2H$, —$CH_2O(CH_2)_2OCH_2CO_2H$, —$(CH_2)_3O(CH_2)_2OCH_2CO_2H$, —$(CH_2)_2O(CH_2)_3OCH_2CO_2H$, —$(CH_2)_2O(CH_2)_2OCH_2CO_2H$ —$CH_2O(CH_2)_3OCH_2H$, and especially —$(CH_2)_6$—$CO_2H$ and particularly —$CH_2$—$CH\!=\!CH$—$(CH_2)_3$—$CO_2H$, as well as amide, ester and salt derivatives of these groups.

Although the group $CV(R^2)$—$NV'R$ of the compounds (I) may take either the form $CH(R^2)$—$NHR$ or the form $C(R^2)\!=\!NR$ the first form is of lesser interest when $R^2$ is other than hydrogen and, irrespective of the nature of $R^2$, the second form is generally the more preferred.

Compounds in which the group $R^2$ is not hydrogen more usually contain aliphatic and araliphatic groups of the type described hereinafter in relation to the group $R^3$, aliphatic hydrocarbon groups substituted directly by an aromatic group, for example an unsubstituted or substituted phenyl or pyridyl group, and particularly unsubstituted aliphatic hydrocarbon groups being of most interest. When the group $R^2$ contains an aliphatic hydrocarbon group directly substituted by an aromatic group, then it is preferred that the aromatic group is not attached to a carbon atom of the aliphatic group which is itself attached directly to the carbon atom of the group $CV(R^2)$—$NV'R$. Thus, for example, a 2-phenylethyl group is preferred to a 1-phenylethyl or phenylmethyl (benzyl) group. The size of the group $R^2$ can however influence the ease with which the compounds may be prepared and $R^2$ is preferably either hydrogen or one of the smaller alkyl groups, for example of 1 to 3 carbon atoms, in substituted form, or particularly in unsubstituted form, for example ethyl and especially methyl.

As regards the group R, groups of the form —$NH.CS NH$—$R^3$ are preferred to those of the from —$NH.CO.NH$—$R^3$. As indicated hereinbefore, the group $R^3$ can be of various forms. Aliphatic hydrocarbon groups constituting $R^3$ may conveniently be acyclic or cyclic and one to five, six, seven, eight, nine, ten, eleven, twelve or even more carbon atoms. Saturated groups are of particular interest, for example an alkyl group which may be branched or unbranched such as methyl, ethyl, propyl, butyl t-butyl, isobutyl, amyl, hexyl, isohexyl, heptyl, 4,4-dimethylpentyl, octyl, 2,2,4-trimethylpentyl, nonyl, decyl, undecyland dodecyl, a cycloalkyl group such as cyclopentyl, cyclohexyl and cycloheptyl, and combinations of alkyl and cycloalkyl groups such as cyclohexylmethyl. Of particular interest are the cyclohexylmethyl group and alkyl groups of 5 to 10 carbon atoms. Aliphatic hydrocarbon groups $R^3$ are perhaps of most interest in the case of groups of the form $CH(R^2)$—$NHR$.

In general, however, aromatic groups constituting $R^3$ are of greater interest than the unsubstitued aliphatic hydrocarbon groups and may be hydrocarbon or heterocyclic groups which may be unsubstituted or substituted. Moreover, the term 'aromatic group' as used herein extends to groups derived from ring systems having aromatic properties but in which the $\pi$-electron system is not fully delocalised over the entire ring system, such groups including those derived from fluorene and the dibenzocyclohexanes and dibenzocycloheptanes, such as 1,2,4,5-dibenzocyclohexane and 1,2,4,5-dibenzocycloheptane, and from dihydrobenzoxazole, dihydrobenzthiazole, N-methyldihydrobenzoxazole and N-methyldihydrobenzthiazole. The heterocyclic groups, which conveniently contain one, two or more similar or different nitrogen, oxygen or sulphur atoms, are more generally linked through a carbon atom so that, in the case of a pyridyl group, for example, pyrid-2-yl, pyrid-3-yl and pyrid-4-yl are of particular interest. Moreover, in the case of those groups containing one or more benzene rings together with one or more non-benzenoid rings, such as those derived from fluorene and from the dibenzocyclohexanes and dibenzocycloheptanes, and from benzthiazole, dihydrobenzthiazole, N-methyldihydrobenzthiazole and thier benzoxazole analogues, linkage of the group is more usually effected through a non-benzenoid ring.

Among the aromatic groups constituting $R^3$, aromatic hydrocarbon groups, for example napthyl (including both napth-1-yl and napth-2-yl) and particularly phenyl, are however generally of rather greater interest than heterocyclic groups. Both aromatic hydrocarbon and heterocyclic groups may be substituted by one or more of various types of substituent, particularly by alkoxy groups, for example those containing alkyl groups of one, two, three or more carbon atoms as described above and especially methoxy, and by substituents being or containing a halogen residue, for example bromo, chloro and especially fluoro, and also halogen substituted alkyl groups such as $CF_3$. Examples of other substituents are sulphamoyl groups which may optionally be N-substituted, amino groups which may be free or substituted, for example dimethylamino, hydroxyl, nitro and alkyl groups, for example of 1 to 3 carbon atoms or otherwise as described above. Substitution may be present at one or more of the ortho, meta and para positions of a phenyl ring or at a combination of two or more such positions (including two ortho or two meta positions), for example at the 2,4- or 3,4-positions. In the case of some substituents, for example nitro, aromatic groups containing a single substituent group may be of particular interest but in other cases substitution by more than one substituent may be of equal or greater interest. It will be appreciated that, in general, substitution and the position of substitution, for example by alkoxy groups and groups being or containing a halogen, may have a definite effect upon the level of activity of a compound.

Although aromatic groups are the preferred type of group $R^3$ other groups $R^3$ also of considerable interest are aliphatic hydrocarbon groups substituted by one or more aromatic groups directly and/or through a sulphur or particularly an oxygen atom. The aliphatic groups may be of a similar size to those described above but preferably comprise an acyclic group, conveniently of 3 carbon atoms, particular of 2 carbon atoms and especially of 1 carbon atom, although this acyclic group may carry a cycloalkyl group as well as an aromatic group. Preferred acyclic groups thus take the form of unbranched alkylene groups such as methylene, ethylene or propylene which link the group $CV(R^2)$—$NV'$—and the aromatic group, or corresponding trivalent groups of similar size. Similar aromatic hydrocarbon and heterocyclic residues are generally of interest for attachment to the aliphatic groups as have already been described above, the aromatic hydrocarbon groups again generally being of rather more interest than the heterocyclic groups. One group $R^3$ containing an aliphatic hydrocarbon group substituted by an aromatic group which is worth particular mention, in addition to those containing phenyl and substituted phenyl groups, is that consisting of an ethyl group substituted at the 1-position by a napthyl group, for example a napth-1-yl group. The reagent N₂N.NH.CO.NHCH(CH₃)-napth-1-yl, which may be used to prepare compounds (I) containing such a group, is of particular interest since it contains an asymmetric carbon atom and may be obtained in optically active form. Heterocyclic groups, where used, are of most interest in this context when linked to the aliphatic hydrocarbon group through a hetero atom, for example pyrid-1-yl. Substitution of an aliphatic hydrocarbon group, particularly terminally, by two or even three aromatic groups, for example phenyl, is of particular interest whilst also of interest are acyclic groups carrying terminally both an aromatic group, for example phenyl, and a cycloalkyl group, for example cyclohexyl. Other substituted aliphatic hydrocarbon groups of especial note, although perhaps less so in the case of groups of the form $CH(R^2)$—NHR, are those which are substituted by an aromatic group through a sulphur or particularly an oxygen atom. In this case, however, the relative instability of the linkages —O—CH₂—S— and —O—CH₂—O must be borne in mind so that, for example, with some forms of group $CV(R^2)$—NV'R any aliphatic hydrocarbon group substituted through oxygen or sulphur is conveniently of at least 2 carbon atoms. Moreover, with groups $R^3$ consisting of an aliphatic hydrocarbon group substituted by more than one aromatic group, these preferably do not have more than one of the aromatic groups attached to the same carbon atom through oxygen or sulphur.

When the group $R^3$ is or contains a substituted aromatic group, some positions of substitution may be of more interest than others in particular cases. Thus, for example, when $R^3$ is a substituted benzyl group the order of interest is often o~>m, when $R^3$ is a substituted phenyloxyethyl group it is o>m>p, and when $R^3$ is a substituted phenyl group it is m~p>o. It will be appreciated that, particularly when two positions are of similar interest, it may be of value to have a substituent at each position, as when the group is 3,4-dimethoxyphenyl.

Examples of specific groups $R^3$ are:

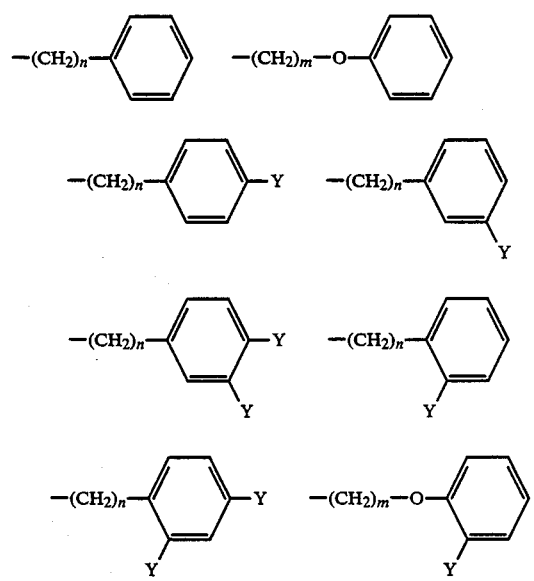

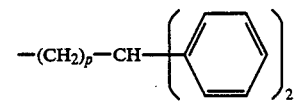

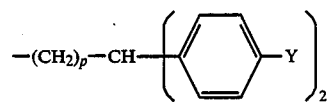

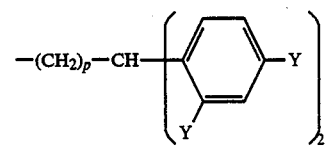

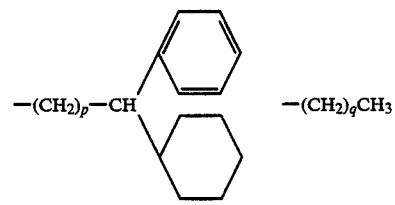

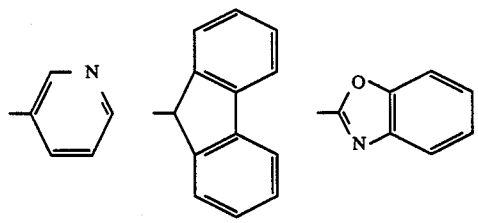

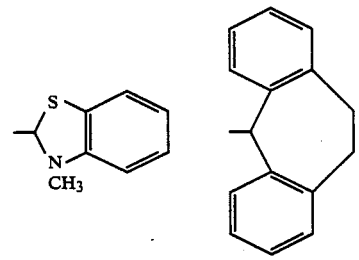

wherein n=0, 1, 2 or 3, m=1, 2 or 3 p=0, 1 or 2, q=1, 2, 3, 4 or 5 and Y=OCH₃, Cl, F, CF₃ or CH₃ (preferences between ortho, meta and para substitution in various cases according to the value of n being indicated hereinbefore).

Compounds of use in the present invention may contain, in the order previously illustrated, one of the following types of ring system: bicyclo [2,2,1] heptane, bicyclo [2,2,1] hept-2Z-ene, 7-oxa-bicyclo [2,2,1] heptane, 7-oxa-bicyclo [2,2,1] hept-2Z-ene, bicyclo [2,2,2] octane, bicyclo [2,2,2] oct-2Z-ene, 6,6-dimethylbicyclo [3,1,1] heptane, cyclohexene, cyclohexane and hydroxycyclopentane, the 6,6-dimethyl-bicyclo [3,1,1] heptane ring system, unlike the others, being substituted in either of two ways, corresponding to reversal of the substituents shown at the a and b positions. It will be appreciated that the bridged ring systems present in compounds according to the present invention show a range of degrees of asymmetry. The 6,6-dimethyl-bicyclo [3,1,1]

heptane ring system is sufficiently asymmetric for reversal of the substituents at the a and b positions to result in a different structural isomer, and thus a different compound (I), both types of compound (I) containing the 6,6-dimethyl-bicyclo [3,1,1] heptane ring system being of use in the present invention. In the case of the bicyclo [2,2,1] heptane and bicyclo [2,2,1] hept-2Z-ene ring systems and their 7-oxa analogues, however, reversal of these substituents would merely provide a structure which represents an alternative stereoisomer, the invention, as has previously been indicated, extending to the use of the compounds (I) in their various stereoisomeric forms. The situation with the bicyclo [2,2,2] oct-2Z-ene ring system is similar to that pertaining in the case of its 7-membered analogue but the bicyclo [2,2,2] octane ring system has a sufficient degree of symmetry for such reversal of the a and b substituents to give the same compound (I) of identical stereochemistry. Among these ring systems, the bridged ring systems are of particular interest and, of those which may be saturated or unsaturated, the former are usually preferred, particularly in the case of the compounds containing an oxygen bridging group, as unsaturation generally confers lower stability whilst the level of biological activity is generally substantially similar. The bicyclo [2,2,1] heptane and bicyclo [2,2,2] octane ring system may be mentioned as of particular interest, and also the corresponding unsaturated ring systems.

It will be appreciated that the structures of the compounds described above provide various opportunities for the occurrence of stereoisomerism. Thus, the substituent groups $R^1$ and $CV(R^2)$—$NV'R$ may be in the cis or trans relationship to each other, compounds of the latter configuration more generally being preferred, although cis compounds (particularly in the 5-exo, 6-exo rather than the 5-endo, 6-endo form as referred to below, where appropriate) are not without interest, particularly in the case of the cyclohexane, cyclohexene and two oxygen bridged ring systems. Moreover, when the ring system is one which is bridged or contains a hydroxy substituent then, in most cases, different isomers will exist which vary according to the way in which the substituent groups $R^1$ and $CV(R^2)$—$NV'R$ are disposed in relation to the bridging groups or the substituent. Isomers of particular interest are shown below one of the two enatiomorphic forms which can generally exist in each case, the other enantiomorph having a structure which is the mirror image of that shown. The unsaturated ring system is illustrated where the ring system may be saturated or unsaturated the symbol B represents —CH$_2$—(position 7), —O—(position 7) or —CH$_2$CH$_2$—(Positions 7 and 8) and the substituent at position b is shown as $C(R^2)$=NR. (The cis isomers can of course also generally exist in two forms for these same ring systems, for example the 5-exo, 6-exo and 5-endo, 6-endo forms for the ring systems containing a group B, each of which forms can again exist as either of two enantiomers.) As indicated above, the bicyclo [2,2,2] octane system possesses a greater degree of symmetry than the other bridged ring systems, as the two bridging groups attached together at the bridge positions (1 and 4) are identical, both being —CH$_2$CH$_2$—. In this case therefore, although the trans isomer is preferred and can exist in two enantiomorphic forms, the endo, exo type of isomerism which can occur with the other bridged ring systems cannot arise.

It will be seen that in the structures shown below the numbering applied herein to the various positions of the ring system has been indicated. It should be noted that the system of numbering adopted for the bridged ring systems which can exist in both saturated form is chosen so that the double bond in the unsaturated ring system receives the lowest number possible (2), the substituents $R^1$ and $C(R^2)$=NR [or $CH(R^2)$—NHR] then being at the 5-and 6-positions respectively. For conformity, a similar system of numbering is followed for the analogous saturated ring systems, the substituents again being described as at the 5-and 6-, rather than the 2- and 3-positions as in the 6,6-dimethyl [3,1,1] heptane system.

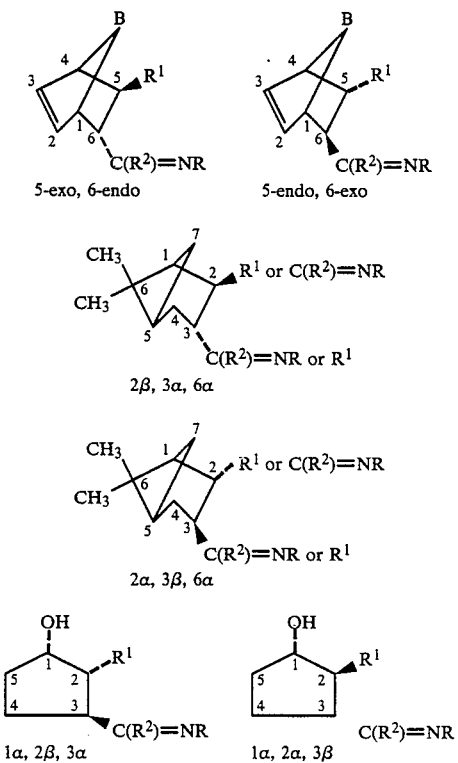

Among the isomers illustrated above, of the two forms shown in each case one is usually preferred to a somewhat greater extent than the other. In the case of the 5-exo, 6-endo and 5-endo, 6-exo isomers the latter is most usually preferred but in the case where B is —O— the 5-exo, 6-endo isomer may be of equal or greater interest. In the case of the 2β, 3α, 6α and 2α, 3β, 6α, 6α isomers the latter is of most interest. [The convention applied herein for naming the compounds (I) containing a 6,6-dimethylbicyclo [3,1,1] heptane ring system is the use of α and β to indicate the directions in which the substituents at the 2 -and 3-positions are directed. In the designations used above the position of the bridging carbon atom at position 6 has for simplicity has also been indicated by an α or a β (the position of the gem dimethyl groups at the 6-position is dictated by that of the carbon atom to which they are attached).] In the case of the 1α, 2β, 3α and 1α, 2α, 3β isomers the latter is again of most interest.

Where the substituent $R^1$ is a 6-carboxyhex-2-enyl group or a group modified therefrom but still containing the double bond, then the configuration about this bond is preferably cis (Z) rather than trans (E). In the other substituent, when this is of the form $C(R^2)$=NR syn and anti isomerism is possible about the carbon-nitrogen double bond but the isomers may often be readily interconvertible at room temperature and thus difficult to separate, existing as a mixture which shows biological activity that may, however, derive predominantly from one isomer. In addition to the foregoing isomerism, as indicated previously the compounds of the present invention will in most cases additionally be resolvable into enantiomorphic forms and one among these may be preferred by virtue of biological activity or physical properties. Single enantiomers may be obtained either by the use of an optically active starting material or by resolution of a pair of enantiomorphs.

Examples of specific compounds (I) which may be used in the present invention include the compound

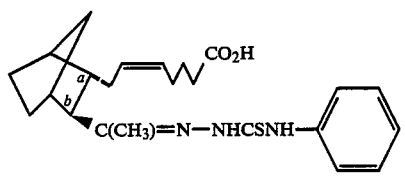

and related compounds in which one or more of the following variations is present: (a) the converse trans stereochemical arrangement of the substituents at a and b; (b) one of the other divalent cyclic groups described hereinbefore in place of the bicyclo [2,2,1] heptane group; (c) a 6-carboxyhexyl, 7-carboxy-6-oxaheptyl- or 6-carboxy-5-oxahexyl group in place of the 6-carboxyhex-2Z-enyl group; (d) derivatisation of the carboxy group as an amide, ester or salt; (e) a grouping —CH=N, —CH$_2$NH—, —CH(CH$_3$)—NH—, —C(C$_2$H$_5$)=N— or —CH(C$_2$H$_5$)—NH— in place of the grouping —C(CH$_3$)=N—; and (f) a n—hexyl or n—heptyl group or a phenyl group which is substituted, for example by one or more groups which are selected from alkyl, alkoxy, amino, halogen, halogen-substituted alkyl, nitro and sulphamoyl groups, in place of the unsubstituted phenyl group.

It will be appreciated that although the thromboxane antagonist prostaglandins of formula (I) are the preferred compounds for use in the present invention, as discussed hereinbefore the invention nevertheless extends to the use of other thromboxane antagonists and in particular those others which are the subject of the four UK patents previously referred to and modifications thereof, including those described in UK patent application 2119375 and European Pat. applications 0094792 and 0107995. These other thromboxane antagonists related to those of formula (I) which are of most interest fall into two groups, the first of which comprises a compound of formula (II)

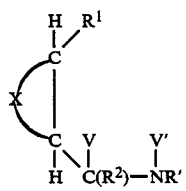 (II)

wherein

$R^1$, $R^2$, V and V' are as previously defined and R' is a group —OR$^3$, —OR$^4$, —D—R$^3$, —N=R$^5$ or —NW.G.W' in which D is —NH—, —NH.CS—, —NH.CO—, —NH.CO.CH$_2$N(R$^6$)—NH.SO$_2$—, —NH.CO.O— or —NH.CS.O—, G is —CO— or —CS— and W and W' together are a group —(CH$_2$)$_d$— in which d is 3,4 or 5, $R^3$ is an aliphatic hydrocarbon group, an aromatic group or an aliphatic hydrocarbon group substituted by one or more aromatic groups directly or through an oxygen or sulphur atom, $R^4$ is an aliphatic hydrocarbon group which is substituted through an oxygen atom by an aliphatic hydrocarbon group which is itself substituted directly by one or more aromatic groups, $R^5$ is an aliphatic hydrocarbon group, an aromatic group in which the π-electron system is not fully delocalised over the entire ring system, or an aliphatic hydrocarbon group substituted by one or more aromatic groups directly or through an oxygen or sulphur atom, and $R^6$ is hydrogen, an aliphatic hydrocarbon group, an aromatic group or an aliphatic hydrocarbon group substituted by one or more aromatic groups directly or through an oxygen or sulphur atom.

Among these compounds of formula (II) preferences as to

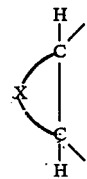

$R^1$, $R^2$, V and V' are broadly as expressed hereinbefore in relation to the compounds of formula (I). However, although the group CV(R$^2$)—NV'R' of the compounds may again take either the form CH(R$^2$)—NHR' or the form C(R$^2$)=NR' for all forms of R', compounds of the first form are of relatively less interest when R is —N=R$^5$ or —NW.G.W'. Preferences as to the group R' are as expressed in UK Pat. No. 2081258 and in its equivalents in relation to the group R of the compounds (I) described therein and also in UK Pat. application 2119375 and European Pat. applications 0094792 and 0107995. In particular, the groups R' of most interest are —OR$^3$ and —D—R$^3$ where D is —NH.SO$_2$— or particularly —NH.CO—, —NH.CO.O— and especially —NH.CS—or —NH.CS.O —. Variarions among R$^3$ are broadly as expressed hereinbefore in relation to the compounds (I). However, as regards groups R' of the form —NH.CO.O—R$^3$ and —NH.CS.O—R$^3$, these are of most interest when R$^3$ is an aliphatic hydrocarbon group substituted, particularly directly, by one or more aromatic groups or expecially an unsubstituted aliphatic hydrocarbon group. In general, unsubstituted aliphatic hydrocarbon groups R$^3$ are again also of greater interest in the case of groups of the form CH(R$^2$)—NHR', for example in which R' is —OR$^3$, —OR$^4$, —NHCOR$^3$, —NHCSR³, —NHCO.OR³ or —NH.CS.OR³. Preferences as to the stereochemistry of the compounds (II) are broadly as expressed hereinbefore for the compounds (I).

The second group of additional thromboxane antagonist prostaglandins comprises a compound of formula (III)

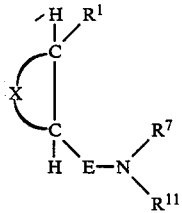
(III)

wherein

and R¹ are as previously defined, E is an aliphatic hydrocarbon group with a chain length between the points of attachment to the divalent cyclic group and to the group NR⁷R" of 1 to 5 carbon atoms or such a group substituted by an aromatic group; R⁷ is hydrogen, an aliphatic hydrocarbon group, an aromatic group or an aliphatic hydrocarbon group substituted directly by an aromatic group or groups; and R" is a group —CO.NR⁸R⁹, —CS.NR⁸R⁹, —CNH.NR⁸R⁹, —CO.R⁹ or —CS.R⁹ in which R⁸ is hydrogen, an aliphatic hydrocarbon group, an aromatic group or an aliphatic hydrocarbon group substituted by an aromatic group or groups, but with the proviso at least one of R⁷ and R⁸ is hydrogen, and R⁹ is an aliphatic hydrocarbon group, an aromatic group or an aliphatic hydrocarbon group substituted directly by an aromatic group or groups and/or through an oxygen or sulphur atom either by an aromatic group or by an aliphatic hydrocarbon group substituted directly by an aromatic group or groups.

Among these compounds of formula (III) preferences as to and R' are as expressed hereinbefore in relation to the compounds of formula (I) whilst preferences as to the groups E, R⁷ and R" are as expressed in UK Pat. 2113678 and in its equivalents in relation to the groups A, R² and R, respectively, of the compounds (I) described therein. Preferences as to the stereochemistry of the compounds (III) are broadly as expressed hereinbefore for the compounds (I).

The compounds (I), (II) and (III) may be prepared by the routes described in the four UK patents referred to hereinbefore and their equivalents and by modifications thereof, or by the procedures described in UK Pat. application 2119375 and European Pat. applications 0094792 and 0107995 and by modifications thereof.

Each of these procedures generally employs an intermediate of formula (IV) in which Y represents R¹ as defined hereinbefore or a precursor therefor and R² is as previously defined.

(IV)

In addition to obtaining such intermediates by the processes described in the patents and patent applications referred to above and by modifications of such processes, an alternative route may be used which is the subject of a UK patent application filed in January 1986 in the names of Jones and Wilson under the title Prostaglandin Synthesis and which is applicable to compounds containing the bicyclo [2,2,1] heptane, bicyclo [2,2,1] hept-2Z-ene, 7-oxa-bicyclo [2,2,1] heptane, 7-oxa-bicyclo [2,2,1] hept-2Z-ene, bicyclo [2,2,2] octane, bicyclo [2,2,2] oct-2Z-ene, cyclohexane and cyclohexene ring systems. The route involves the reaction of a diene and a dienophile to form as a Diels Alder adduct a compound (IV). The route is illustrated below in reaction scheme (1) for a compound (IV) in which the groups Y and C(R²)=O are 6-ethoxycarbonyl-5-oxahexyl and acetyl respectively:

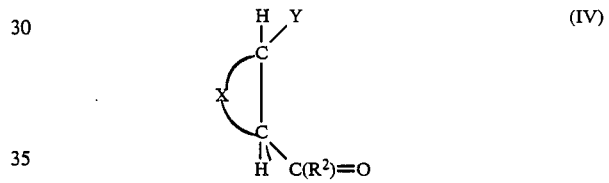

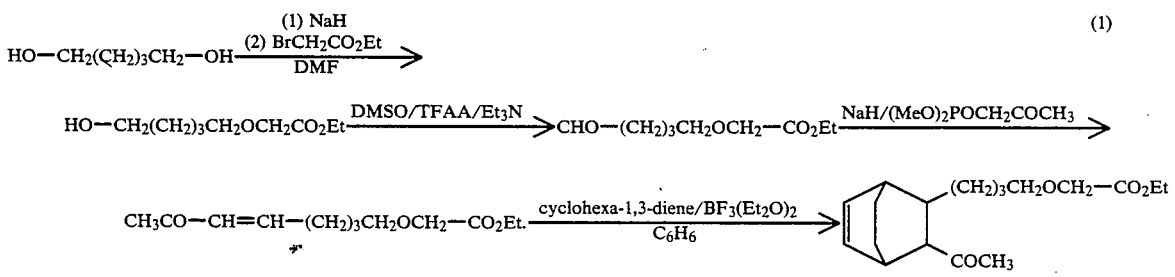

(1)

(In this reaction scheme conventional abbreviations are used in designating the reactants and solvents, i.e.

Me : methyl; Et : ethyl; DMR : dimethylformamide; DMSO : dimethylsulphoxide; TFAA : trifluoroacetic acid anhydride.)

It will be appreciated that the ring system produced by such a procedure contains a double bond and that a reduction step will be required in order to produce a saturated ring system. It should be noted that the Horner reaction using the phosphonate reagent will generally provide a dienophile having the trans configuration about the carbon-carbon double bond so that this route is particularly adapted to the preparation of compounds in the preferred trans form, although the route can be used for the preparation of compounds (I) of the cis configuration if a different approach is used to provide a cis dienophile. Moreover, the Diels Alder reaction will lead to a mixture of the two trans or cis isomers which can exist in most cases and a separation will be necessary if one of these is required free from the other. This is not the case, however, with the bicyclo [2,2,2] octane, cyclohexane and cyclohexene ring systems which have a greater degree of symmetry and therefore exist in only one trans and one cis form (which do however each consist of two enantiomers). The route has the particular advantage that it may be used to produce directly an intermediate (IV) containing the desired group Y, subject to modification of the terminal carboxy group from or to derivature form, rather than having to build up the group Y after construction of the ring system as in the other procedures. The Diels Alder reaction may use only heat but can then be rather slow so that it is often more convenient to utilise a Lewis acid as a catalyst, for example alumium chloride or more preferably titanium tetrachloride, stannic chloride or especially boron trifluoride, although it is still also preferred to carry out the reaction at elevated temperature, for example at about 80° C. It will be clearly apparent to those skilled in the art how the diene and dienophile used in the scheme shown above may be varied to produce different compounds (IV). Thus, firstly, pentadiene, furan or buta-1,3-diene can be used in the final step as the diene in place of cyclohexa-1,3-diene. secondly, the phosphonate reagent used in the Horner reaction may be varied through replacing the terminal acetyl group by an alternative acyl group or a formyl group in order to produce dienophiles providing a compound (IV) containing an alternative group $R^2$. The third form of variation of the procedure shown involves the use of a different compound in the reaction with this phosphonate reagent to produce dienophiles providing a compound (IV) containing an alternative group Y. Thus, it will be apparent that the use of a diol HO—CH$_2$—(CH$_2$)$_4$CH$_2$—OH will provide a compound (IV) containing a 7-ethoxycarbonyl-6-oxaheptyl group Y and further variations of particular interest are illustrated in reaction schemes (2) and (3) below

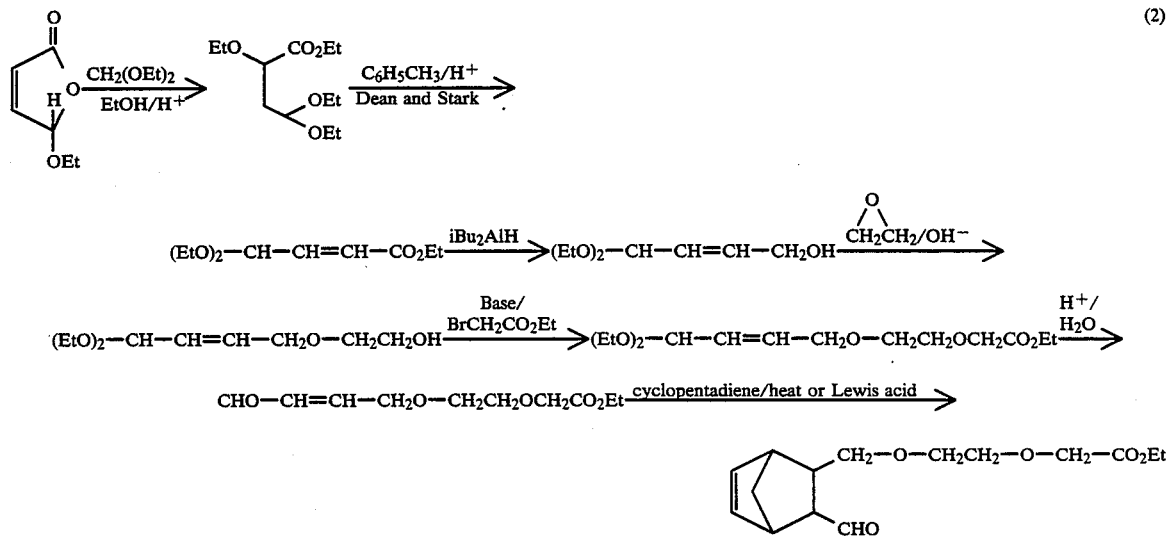

(2)

The procedure can be varied through chain extension of compound (EtO)$_2$—CH—CH=CH—CH$_2$ OH, for example via the corresponding nitrile, before the reaction with ethylene oxide. Thus, for example, a single chain extension will give an aldehyde/ester CHO—CH=CH—CH$_2$CH$_2$O—CH$_2$CH$_2$OCH$_2$CO$_2$Et. Alternatively, or additionally the formyl group in the dienophile may be replaced by a group $R^2$CO—, this being effected in several possible ways, the formyl group conveniently being oxidised to a carboxy group which is then converted to the acid chloride, which is in turn converted to an acyl group, for example by reaction with the appropriate cadmium compound $(R^2)_2$Cd, dimethylcadmium providing an acetyl group.

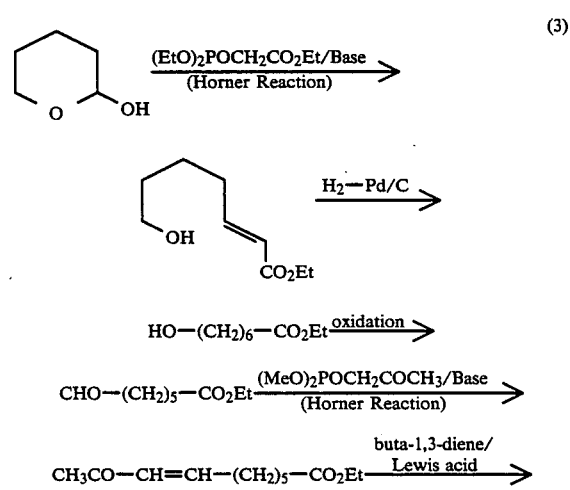

(3)

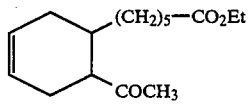

The corresponding compounds containing a 5- or 7-membered ring system may be used in place of the 2-hydroxytetrahydropyran as a starting material to provide compounds $CH_3CO-CH=\!=\!-(CH_2)_4-CO_2Et$ and $CH_3CO-CH=\!=\!CH-(CH_2)_6-CO_2Et$.

The preparation of compounds having a group $R^1$ containing an oxygen atom at the 5-position containing the 6,6-dimethylbicyclo [3,1,1] heptane and hydroxycyclopentane systems is most conveniently effected by modifications of procedures described in UK Pat. 2081258 for the preparation of compounds with a side chain having an oxa group at the 3-position, for example by chain extension (−)-myrtenol and (−)-nopol. With these rings systems, when a compound containing a group $R^2$ other than hydrogen is required, the corresponding intermediate compound (IV) containing a formyl group will usually be prepared and then converted to the compound containing the desired group $C(R^2)=\!=O$ through a Grignard reaction.

Compounds containing thio rather than oxa groups can be prepared by modifications of the procedures described for the former. Moreover, it will be appreciated that the methods described above for the preparation of the compounds (I), (II), (III) and (IV) are not the only ones which may be used for the preparation of these compounds and that various alternative procedures may be used as will be apparent to those skilled in the art of prostaglandin chemistry.

In the case of the compounds of formulae (I) and (II), these may be obtained from the intermediate (IV) by reacting it with a reagent $ZNH_2$, Z being either R or R′ or a precursor therefor, using procedures described in UK Pat. Nos. 2039909, 2039480 and 2081258, and where appropriate converting the group Y and/or the group Z in the resultant product into the groups $R^1$ and R or R′, respectively. In the case of compounds (I) and (II) in which the group $CV(R^2)-NV'R$ is of the form $C(R^2)=\!=NR$, this group can usually be formed through direct reaction of the group $C(R^2)=\!=O$ of the intermediate compound (IV) with a reagent $RNH_2$. Thus, the compounds in which R is $-NH.CS.NH-R^3$ are readily obtained by reaction with the appropriate thiosemicarbazide $H_2N.NH.CS.NH.R^3$. These procedures are described particularly in UK Pat. Nos. 2039909, 2039480 and 2081258 and in UK Pat. application 2119375. In the case of compounds (I) and (II) in which the group $CV(R^2)-NV'R$ is of the form $CH(R^2)-NHR$, the compound containing the corresponding group $C(R^2)=\!=NR$ is most usually prepared first and then reduced to the desired compound. Various methods of reduction are available, the choice depending largely upon whether the compound contains any carbon-carbon double bonds. When this is not the case hydrogenation using a palladium/charcoal or like catalyst is appropriate but when a carbon-carbon double bond is present in the ring or in the group $R^1$ a reducing agent such as sodium cyanoborohydride is required which will not effect reduction of that carbon-carbon double bond. If desired, it is possible to prepare compounds (I) containing a saturated bicyclo [2,2,1] heptane, 7-oxa-bicyclo [2,2,1] heptane or bicyclo [2,2,2] octane ring systems and a group $CV(R^2)-NV'R$ of the form $CH(R^2)-NHR$ through the reduction of the corresponding bicyclo [2,2,1] hept-2Z-ene, 7-oxa-bicyclo [2,2,1] hept-2Z-ene or bicyclo ([2,2,2] oct-2Z-ene containing side chains Y and $C(R^2)=\!=NR$ followed, where appropriate, by the conversion of Y to the desired group R′. These reduction procedures are described particularly in European Pat. applications 0094792 and 0107995. In the case of the compounds of formula (III) the group $C(R^2)=\!=O$ of the intermediate compound (IV) is modified further, as described in UK Pat. No. 2113678, before conversion to the compound (IV).

For the sake of convenience, only, the use of thromboxane antagonists in the present invention is described hereinafter in relation to the compounds (I) but it will be appreciated that the other thromboxane antagonists may be used in an exactly similar manner to the compounds (I).

The compounds (I) are of interest in the treatment of neoplasias in different forms of hormone-dependent tissue, for example neoplasias of androgen-dependent tissues such as those of the prostrate, but the present invention is of particular interest for the treatment of neoplasias of oestrogen-dependent tissues.

Although they are also of potential interest for use alone, the compounds (I) are of particular interest for use in conjunction with various of the types of agent of value in hormone therapy, particularly that of oestrogen-dependent tissues, including oestrogen antagonists, for example the compound tamoxifen or trans-1-[4-(2-dimethylaminoethoxy)-phenyl]-,2-diphenylbut-1-ene, inhibitors of the enzyme aromatase which is involved in the generation of oestrogen in vivo, for example 4-hydroxyandrostene-3,17-dione, and compounds which control oestrogen production, conveniently as antagonists rather than stimulants, through interaction in other parts of the endocrine system, for example analogues of gonadotrophin releasing hormone (Gn—RH or LHRH), and also progestogens, anti-androgens and inhibitors of the biosynthesis of adrenocortical steroids, for example aminoglutethimide.

Alternatively, or additionally if appropriate, the compounds (I) are of particular interest for use in conjunction with various of the types of cytotoxic agent including the biological alkylating agents, for example the chloroethylamines mustine, chlorambucil and melphalan, the antimetabolites, for example methotrexate and other quinazolines, the purine analogues, for example 6-mercaptopurine purine and 2-amino-6-mercaptopurine, the pyrimidine analogues, for example 5-fluorouracil and cytosine arabinoside, the cytotoxic antibiotics, for example actinomycins such as dactinomycin and anthracyclines such as daunorubicin, doxorubicin, and bleomycin, the plant alkaloids, for example vinca alkaloids such as vinblastine, vincristine and vindesine, and other drugs such as dibromomannitol, hydroxyurea, procarbazine, 1-asparaginase, deoxycoformycin, cisdiaminodichloroplatinum, hexamethylmelamine and the interferons.

Accordingly the present invention further comprises products containing a compound of formula (I), as defined hereinbefore, and one or both of a hormonal therapy agent and a cytotoxic agent for simultaneous, separate or sequential use in the treatment of hormone-dependent neoplasias.

The compounds (I) may be utilised in the manufacture of products for use as medicaments in mammals (animals and particularly humans) by a variety of methods, the medicament usually comprising a formulation of one or more of the compounds (I) together with a physiologically acceptable diluent or carrier. The compounds may, for instance, be applied as an aqueous or oily solution or as an emulsion for parenteral administration, the composition therefore preferably being sterile and pyrogen-free. The preparation of aqueous solutions of the compounds may be aided by salt formation, although aqueous solubility does vary among the different compounds (I), the oxygen-bridged compounds, for example, having a higher water solubility than the corresponding carbon-bridged compounds. The compounds may also be compounded for oral administration, most usually in the presence of conventional solid carrier materials such as starch, lactose, dextrin and magnesium stearate. Alternative formulations which may be considered are as aerosols, suppositories, cachets, and, should localised treatment be appropriate, as a suitable topical fomulation which will usually be sterile and may also be pyrogen-free, for example in the form of creams or drops.

When, as is more often the case, the compounds (I) are used in combination therapy, they will usually be administered either before or together with the hormonal therapy agent or cytotoxic agent, the choice depending to some extent on the particular agent used. In the former usage both the compound (I) and the agent will each be formulated separately, usually in a conventional manner, for example both being formulated as described above, although the two compositions may be packaged together for ease of sequential administration to the patient. In the latter usage the compound (I) and the agent may also be formulated separately but it may be preferred to include the compound (I) and the agent in the same composition. Such a pharmaceutical composition may again conveniently take one of the physical forms described above for compositions containing only the compound (I) and may, if desired, contain more than one compound (I) and/or more than one agent. Where more than one agent is present these will usually be of one type or the other, although the use of both a hormonal therapy and a cytotoxic agent is not excluded.

The present invention thus includes a pharmaceutical composition which comprises a compound of formula (I), as defined hereinbefore, and one or both of a hormonal therapy agent and a cytotoxic agent, together with a physiologically acceptable diluent or carrier.

The compositions used in the present invention may conveniently be in unit dosage form, i.e. in portions containing a unit dose or a multiple or subunit thereof. As regards the dosages given, these will usually be similar to those conventionally used for the hormonal therapy or cytoxic agent, although it may be possible to reduce the levels somewhat in view of the enhancement of effect achieved due to the use of the compounds (I). Such dosages in mg per kilogram or daily quantity terms will vary from one agent to another but are well documented in the pharmaceutical literature, for example in the 1984–5 Data Sheet Compendium of the Association of the British Pharmaceutical Industry (Datapharm Publications Limited, London, England). Thus, in the case of tamoxifen, for example, the recommended dosage range in the treatment of breast cancer is from 20 to 40 mg of tamoxifen daily, usually given in two spaced equal doses. In the case of the cytotoxic agent melphalan, for example, the recommended dosage for the treatment of ovarian adenocarcinoma is 0.2 mg/kg body weight daily, usually given in three spaced equal doses, over a period of 5 days whilst for the treatment of advanced carcinoma of the breast it is 0.2–0.3 mg/kg body weight daily over a period of 4–6 days.

As regards the dosage of the compounds (I), it is difficult to give a rigid definition of dosage as this will depend in part on the specific compound (I) used, the hormonal therapy or cytotoxic agent with which it is used, the method of formulation and mode of administration. However, some general guidance may be given. In the case of systemic administration the normal dosage proposed for use on each day of therapy lies in the range from about 0.1 mg to about 10 mg per kilogram (the average weight of a human being about 70 kg) and particularly from about 1 mg to about 5 mg per kilogram. It will be appreciated, however, that dosages outside this range may be considered, for example should localised application be appropriate, and that the daily dosage may be divided into two or more portions. [When the thromboxane antagonists other than the compounds (I) are used the dosage may of course vary quite considerably depending upon the particular antagonist employed. However, for the compounds (II) and (III) the dosage range is broadly similar as it will also be with many other antagonists, although an increase in the dosage level, for example up to 20 or even 50 mg per kilogram, may be required for the weaker antagonists.]

The present invention therefore further includes a method for aiding the regression and palliation of neoplastic disease in hormone-dependent tissues which comprises administering to a patient in need thereof amounts which together are therapeutically effective in achieving such regression and palliation of a compound of formula (I) as defined herein and of one or more of a hormonal therapy agent and a cytotoxic agent.

As indicated, although the invention is also of particular interest in the case of oestrogen-dependent tissue, for example prostrate tissue, most commonly the tissues treated are oestrogen-dependent, particularly being mammary or uterine tissue, and the neoplastic disease is usually a carcinoma (including adenocarcinomas). Administration is usually parenteral or more preferably oral. As indicated hereinbefore, the compound (I) will usually be given with, or before, the agent, a suitable time lapse where the latter approach is used being from about 1 hour to 4 hours, for example 2 or 3 hours. It is, however, possible and indeed it is often usual to administer a series of doses of the agent. In such a case it may not be necessary for each administration of the agent to be made concomitantly with, or at the interval given above after the administration of the compound (I). It may be possible to administer the compound (I) alone or together with the agent, followed by one or more repeated spaced doses of the agent alone. If the treatment is continued over an extended period repeat doses of the compound (I) are also likely to be required and one possible regimen would involve the administration of the agent alone on certain occasions and together with the compound (I) on others.

It will be appreciated that thromboxane antagonists, and in particular the compound (I), may also be of value in other contexts not associated with neoplastic disease where an increase in blood flow to uterine tissue or a decrease in the growth of uterine tissue is desired, for example in hypotensive pregnancy.

The invention is illustrated by the following Examples. After the Examples a set of Preparations is given describing the production of certain alternative compounds (I) of particular interest whose preparation is not already described in the published literature.

EXAMPLES

Example 1

Formulation

The following formulations illustrate pharmaceutical compositions of the invention which may be prepared:

|  | per tablet w/w |
| --- | --- |
| Compound (I) (micronised) | 19.3% |
| Tamoxifen (micronised) | 64% |
| "Avicel" (microcrystalline cellulose) | 12.7% |
| Polyvinylpyrrolidone | 1% |
| Alginic acid | 2% |
| Magnesium stearate | 1% |

The compound (I), for example (±)-5-endo-(6'-carboxyhex-2'Z-enyl)-6-exo-(1'-[N-(phenylthiocarbamoyl)-hydrazono]-ethyl)-bicyclo [2,2,1] heptane, and the tamoxifen are mixed with the "Avicel" and the polyvinyl pyrrolidone is added, dissolved in sufficient industrial methylated spirits (74° OP) to produce a mass suitable for granulating. The mass is granulated through a 20 mesh sieve (British mesh standard) and the resultant granules dried at a temperature not exceeding 50° C. The dried granules are passed through a 20 mesh sieve and the alginic acid and magnesium stearate then added and mixed with the granules. The product is then compressed into tablets.

By the same method the following formulation is prepared:

|  | per tablet w/w |
| --- | --- |
| Compound (I) (micronised) | 22.5% |
| Melphalan (micronised) | 40% |
| "Avicel" (microcrystalline cellulose) | 33.5% |
| Polyvinylpyrrolidone | 1% |
| Alginic acid | 2% |
| Magnesium stearate | 1% |

A further tablet formulation is as follows:

|  | per tablet w/w |
| --- | --- |
| Compound (I) (micronised) | 29.3% |
| Melphalan (micronised) | 54% |
| Lactose (300 mesh) | 6.3% |
| Maize starch | 5% |
| Gelatine | 3.3% |
| Magnesium stearate | 2% |

These tablets may be prepared by mixing the compound (I), for example (±)-5-endo-(6'-carboxyhex-2'Z-enyl)-6-exo-(1'-[N-(phenylthiocarbamoyl)-hydrazono]-ethyl)-bicyclo [2,2,1] heptane, and the melphalan with the lactose and half the total quantity of maize starch required, then adding to the mass a 5% w/v solution of the gelatine in water. The product is granulated through a 16 mesh sieve and the resultant granules are dried to constant weight at a temperature not exceeding 60° C. The dried granules are passed through a 20 mesh sieve and mixed with magnesium stearate and the remainder of the maize starch. The product is then compressed into tablets.

An injectable solution is prepared as follows:

The compound (I) of the invention in acid form (1 part by weight) and tamoxifen (3.3 parts by weight) are dissolved in 100 ml of 0.9% w/v aqueous NaCl containing sufficient NaOH or other suitable base for neutralisation of the compound (I).

Example 2

Tests of action of (±)-5-endo-(6'-carboxyhex-2'Z-enyl)-6-exo-(1'-[N-(phenylthiocarbamoyl)-hydrazono]-ethyl-bicyclo [2,2,1] heptane on uterine tissue in the ovariectomised rat Sexually mature virgin female rats of the CD strain (Sprague-Dawley derived) weighing 220–366 grams were used in these tests. The rats were ovariectomised, the ovaries, fallopian tubes and some of the surrounding fat being removed and the uterine horn returned into the abdominal sac. Each rat was then allowed at least 14 days to recover.

(1) In a first set of tests, two doses of the compound (I) (±)-5-endo-(6'-carboxyhex-2'Z-enyl)-6-exo-(1'-[N-(phenylthiocarbamoyl)-hydrazono]-ethyl)-bicyclo [2,2,1] heptane, were administered intravenously in an aqueous sodium hydroxide (M/400)/sodium chloride (0.9% w/v) vehicle at a dosage level of 5 mg/kg and at an interval of 1 hour 40 minutes to each of a group of 6 rats. A second, control group of 6 rats received no treatment. Measurements were made of the uterine blood flow using the microsphere (15 μm NEN-Trac) technique (Phaily and Senior Journal of Reproduction and Fertility, 1978, 53, page 91), this being applied 3 hours and 10 minutes after the first administration of the compound. This procedure showed that the compound had no significant effect on uterine blood flow as compared with the untreated control group and, although the compound did cause a slight reduction in uterine wet weight corresponding with a decrease in the water content of the uterus, the decreases were not statistically significant when compared with the control group. Similarly, a slight fall was seen in uterine dry weight after treatment with the compound but this was again statistically non-significant as compared with the control group. These results are to be expected since the rats are ovariectomised and no separate supply of oestrogen is provided in the tests.

(2) In a second set of tests, two doses of the same compound (I) were administered intravenously in an aqueous sodium hydroxide (M/400)/sodium chloride (0.9% w/v) vehicle at a dosage level of 5 mg/kg to each of a group of 6 rats. The two doses were spaced at an interval of 1 hour 40 minutes with an intervening intravenous administration of 0.5 μg/kg of 17β-oestradiol (17B-E$_2$) in 10% v/v propylene glycol in distilled water being given 10 minutes after the first administration of the compound. Once again, a second control group of 8 rats was used which in this case received the 17β-oestradiol but none of the compound. The measurements made were similar to those of the first set of tests, being made 3 hours and 10 minutes after the first administration of the compound. The results obtained are shown in Tables 1 and 2 from which it will be seen that the use of the compound (I) produced a significant (P<0.005) increase in the uterine blood flow response to 17β-oestradiol, this increase corresponding with an increase in cardiac output to the uterus. The use of the compound also caused a significant (P<0.005) decrease in both the uterine wet and dry weight responses to 17β-oestradiol, the fall in uterine wet weight corresponding with a decrease in uterine water content.

the compound but not to a statistically significant extent.

TABLE 1

| | | | Uterine blood flow | | | |
|---|---|---|---|---|---|---|
| | Number of rats | Cardiac output (ml/min) | Uterine blood flow | | % Cardiac output to uterus | |
| Pretreatment | | | (ml/min) | (ml/min/100 g) | (ml/min) | (ml/min/100 g) |
| 17β-E$_2$ alone (Control) | 8 | 104 ± 11 | 0.94 ± 0.10 | 735 ± 66 | 0.92 | 688 |
| Compound (I) | 6 | 109 ± 7 | 1.33 ± 0.19 | 1438 ± 193[1] | 1.23 | 1342 |

[1] $p < 0.005$

TABLE 2

| | | | Uterine weight | | | |
|---|---|---|---|---|---|---|
| Pretreatment | Number of rats | Rat weight (g) | Uterine weight | | Water content expressed as | |
| | | | Wet | Dry | (mg) | (% of wet weight) |
| 17β-E$_2$ alone (Control) | 8 | 321 ± 7 | 128 ± 7 | 35 ± 2 | 93.0 | 72.6 |
| Compound (I) | 6 | 353 ± 15 | 93 ± 8[1] | 26 ± 2[1] | 67.3 | 72.1 |

[1] $p < 0.005$

TABLE 3

| | | | Uterine blood flow and weight | | | | |
|---|---|---|---|---|---|---|---|
| Treatment | Number of rats | Weight of rats (g) | Cardiac output (ml/min) | Uterine blood flow (ml/min/100 g) | Uterine weight (mg) | | Water content (% of wet weight) |
| | | | | | Wet | Dry | |
| 17β-E$_2$ alone (Control) | 8 | 344 ± 11 | 113 ± 12 | 535 ± 102 | 99 ± 5 | 30 ± 4 | 67 |
| 17β-E$_2$ + Compound (I) | 12 | 357 ± 9 | 110 ± 6 | 890 ± 119[1] | 92 ± 12 | 22 ± 2[1] | 76 |

[1] $p < 0.005$

TABLE 4

| | Blood flow to other organs | | | | | | | | |
|---|---|---|---|---|---|---|---|---|---|
| Treatment | Liver | Lung | Kidney (R) | Kidney (L) | Stomach | Adrenal (R) | Adrenal (L) | Duodenum | Spleen |
| 17β-E$_2$ alone (Control) | 18 ± 5 | 55 ± 21 | 624 ± 64 | 677 ± 93 | 50 ± 7 | 851 ± 113 | 814 ± 104 | 327 ± 62 | 177 ± 22 |
| 17β-E$_2$ + Compound (I) | 13 ± 2 | 46 ± 9 | 624 ± 40 | 614 ± 39 | 48 ± 6 | 589 ± 63 | 629 ± 82 | 357 ± 22 | 168 ± 22 |

(3) In a third set of tests the same protocol was used as in the second set of tests. It was found that in these tests, which used a different batch of the compound (I), the doses of the compound (I) had to be raised to 10 mg/kg to get a similar effect to that obtained in the second set of tests with a 5 mg/kg dose level. In this set of tests the measurements made were extended to include blood flow to the liver, lungs, kidneys, stomach, adrenals and spleen. The uterine data is presented in Table 3 and the data for the other organs in Table 4.

It will be seen from Table 3 that, at 10 mg/kg, the compound (I) again produced a significant increase in the uterine blood flow response to 17β-oestradiol together with a significant fall in the dry weight, although not the wet weight, of the uterus, as compared with that observed for 17β-oestradiol used alone. Table 4 shows that there was in general no difference within the range of error, in the blood flow through the other organs when using 17β-oestradiol alone or together with the compound (I). The one exception to this is adrenal blood flow which is found to decrease in the presence of

Example 3

Tests of action of (±)-5-endo-(6'-carboxyhex-2'2-enyl) -6-exo-(1'-[N-phenylthiocarbamoyl)-hydrazono]-ethyl)- bicyclo [2,2,1] heptane on uterine tissue in the normal proestrous rat Sexually mature virgin female rats of the CD strain (Sprague-Dawley derived) weighing 274–327 grams were used in these tests. These rats were not ovariectomised and were in the proestrous phase of the oestrus cycle. The protocol of Example 2(3) was used with the modification that, as the rats had not been ovariectomised, no administration of 17β-oestradiol is required.

The results are shown in Tables 5 and 6 from which it will be seen that a significant increase in uterine blood flow resulted, together with a decrease in uterine weight which was not however statistically significant. As in Example 2(3) there was in general no difference, within the range of error, in the blood flow through the other organs in the central when using the compound (I). It should be noted that in this case the values for adrenal blood flow are higher when using the compound but, again, not to a statistically significant extent.

TABLE 5

Uterine blood flow and weight

| Treatment | Number of rats | Weight of rats (g) | Cardiac output (ml/min) | Uterine blood flow (ml/min/ 100 g) | Uterine weight (mg) Wet | Uterine weight (mg) Dry | Water content (% of wet weight) |
|---|---|---|---|---|---|---|---|
| None (Control) | 6 | 285 ± 14 | 121 ± 14 | 155 ± 32 | 329 ± 33 | 67 ± 5 | 79 |
| Compound (I) | 6 | 303 ± 24 | 116 ± 6 | 512 ± 105[(2)] | 305 ± 18 | 58 ± 3 | 80 |

[(2)] $P < 0.01$

TABLE 6

Blood flow to other organs

| Treatment | Ovaries | Liver | Lung | Kidney (R) | Kidney (L) |
|---|---|---|---|---|---|
| None (Control) | 419 ± 46 | 13 ± 3 | 35 ± 6 | 544 ± 47 | 537 ± 31 |
| Compound (I) | 541 ± 86 | 22 ± 5 | 36 ± 3 | 671 ± 50 | 661 ± 82 |

| Treatment | Stomach | Adrenal (R) | Adrenal (L) | Duodenum | Spleen |
|---|---|---|---|---|---|
| None (Control) | 66 ± 11 | 736 ± 182 | 693 ± 180 | 391 ± 48 | 285 ± 24 |
| Compound (I) | 71 ± 4 | 917 ± 141 | 941 ± 185 | 276 ± 72 | 272 ± 59 |

PREPARATION OF ALTERNATIVE COMPOUNDS (I)

(A) Preparation of trans-5-(6'-carboxy-5'-oxahexyl)-6-(1'-[N-(phenylthiocarbamoyl)-hydrazono]-ethyl)-bicyclo [2,2,2] octane (1) Ethyl 8-hydroxy-3-oxa-octanoate A solution of 1,5-pentanediol (50 g, 480 mmol) in 100 ml of dry, redistilled dimethylformamide (DMF), is added dropwise, under nitrogen, to sodium hydride (11.3 g, 480 mmol) in 300 ml DMF (obtained from 19.2 g of a 60% w/v dispersion of sodium hydride in oil by washing with sodium dried petroleum spirit). After the addition is complete (about 45 minutes) the reaction mixture is heated to about 70° C. and stirring is continued for a further 4 hours when all hydrogen evolution has ceased. The reaction mixture is then cooled to 0° C. and ethyl bromoacetate (80.2 g; 480 mmol) is added, the ester being added in one portion in order to minimise ester cleavage by the basic reaction medium. After cessation of the consequent vigorous reaction, the mixture is heated at about 70° C. for a further 2 to 3 hours before the removal of the majority of the solvent by vacuum distillation. On cooling, the residue is poured into water and the product is isolated by ethyl acetate extraction and purified by chromatography on Florisil to provide the title compound as an oil (61.2 g, 67%), $v_{max}$ (film): 3450, 1740, 1195, 1130 cm$^{-1}$.

(2) Ethyl 7-formyl-3-oxaheptanoate

To a solution of dimethylsulphoxide (18.6 ml, 263 mmol) in 75 ml of $CH_2Cl_2$ at −60° C., under nitrogen, is added dropwise a solution of trifluoroacetic anhydride (27.8 ml, 197 mmol) in 75 ml of $CH_2Cl_2$, over about 15 minutes. The reaction mixture is stirred for a further 15 minutes at −60° C. and the hydroxy/ester (1) (25 g, 132 mmol) in 150 ml $CH_2Cl_2$ is then added at such a rate as to keep the reaction temperature below −60° C. (over about 30 minutes). After a further 15 minutes at this temperature, triethylamine (55 ml, 395 mmol) is added slowly over about 15 minutes, the reaction mixture is allowed to warm to ambient temperature (about 1.5 hours) and is then quenched with water. The product is isolated by extraction with dichloromethane and purified by chromatography on Florisil to provide the title compound as an oil (20.7 g, 84%), $v_{max}$ (film) 1750, 1725, 1195, 1130 cm$^{-1}$.

(3) Ethyl 10-keto-8(E)-3-oxa-undecenoate

A solution of dimethyl 2-oxopropyl-phosphonate (10.6 g, 64 mmol) in 50 ml of dry, redistilled tetrahydrofuran (THF) is added over a Period of about 20 minutes to a vigorously stirred suspension of sodium hydride (1.5 g, 64 mmol) in THF (obtained from 2.5 g of a 60% w/v dispersion of sodium hydride in oil by washing with sodium dried petroleum spirit), under nitrogen. The resulting suspension of a flocculant precipitate is stirred for a further 1 hour and the aldehyde/ester (2) (10 g, 53 mmol) in 50 ml THF is then added dropwise. The reaction mixture is stirred for a further 3 to 4 hour at room temperature before quenching with a 1% v/v aqueous solution of acetic acid. The product is isolated by ether extraction and purified by chromatography on silicic acid, the desired fraction being eluted in toluene-/ethyl acetate (90:10 v/v), to provide the title compound as an oil (7.5 g, 62%), $v_{max}$ (film) 1745, 1670, 1620, 1190, 1125 cm$^{-1}$, $\lambda_{max}$ (MeOH) 222 nm, $\epsilon_{max}$ 3488.

(4) 5-endo-(6'-Ethoxycarbonyl-5'-oxahexyl)-6-exo-acetyl-bicyclo [2,2,2] oct-2Z-ene and 5-exo-(6'-ethoxycarbonyl-5'-oxahexyl)-6-endo-acetyl-bicyclo [2,2,2] oct-2Z-ene To a solution of the enone/ester (3) (2.5 g, 11 mmol) in 50 ml of sodium dried benzene is added a catalytic amount of boron trifluoride etherate (0.27 ml; 2.2 mmol), followed by cyclohexa-1,3-diene (2.1 ml; 22 mmol). The resulting solution is refluxed under nitrogen for 4 to 5 hours and, on cooling, the mixture is poured onto a saturated aqueous solution of sodium hydrogen carbonate. The product is isolated by ether extraction and purified by chromatography on Florisil, the desired fraction being eluted in toluene/ethyl acetate (5:5 v/v), to yield the mixture of title compounds as an oil (1.9 g, 56%), $v_{max}$ (film) 1750, 1705, 1195, 1130, 700 cm$^{-1}$, $\delta(CDCl_3)$ 6.35 (1H, dd), 4.16 (2H, q), 4.00 (2H, s), 3.51 (2H, t), 2.75 (1H, m), 2.4 (1H, m), 2.08 (3H, s), 1.92–1.05 (12H, m), 1.28 (3H, t).

(5) trans-5-(6'-Ethoxycarbonyl-5'-oxahexyl)-6-acetyl-bicyclo [2,2,2] octane

The mixture from (4) of 5-endo-(6'-ethoxycarbonyl-5'-oxahexyl)-6-exo-acetyl-bicyclo [2,2,2] oct-2Z-ene and 5-exo-(6'-ethoxycarbonyl-5'-oxahexyl)-6-endo-acetyl-bicyclo [2,2,2] oct-2Z-ene (2.0 g, 65 mmol) is dissolved in ethanol and a catalytic amount of palladium on activated charcoal (10% w/w) is added. The resulting mixture is vigorously stirred under an atmosphere of hydrogen until the uptake of hydrogen is complete. The catalyst is removed by filtration through a Celite plug and the filtrate evaporated to give, as an oil, the title compound in admixture with trans-5-(4'-hydroxy)-6-acetyl-bicyclo [2,2,2] octane in a ratio of 55:45 w/w ester:alcohol[(1)].

[(1)] Better catalytic selectivity in favour of the ester is achieved by the use of Wilkinson's catalyst or ruthenium on carbon.

(6) trans-5-(6'-Carboxy-5'-oxahexyl)-6-acetyl-bicyclo [2,2,2] octane

The mixture from (5) is dissolved in dioxan/water (1:1 v/v) and an aqueous solution of 2M NaOH is added to give a final base concentration of N/20. The reaction mixture is heated for 2.5 hours at about 60° C. then cooled and poured into water. The aqueous phase is washed with ether to remove the alcohol component of the starting material and is then acidified to pH 3–4 and the desired product isolated by ether extraction. The extract is purified by chromatography on silicic acid, the desired fraction being eluted in toluene/ethyl acetate (85:15 v/v), to yield the title compound as an oil (1.9, 56%), $\nu_{max}$ (film) 1750, 1705, 1195, 1130, 700 cm$^{-1}$, $\delta$(CDCl$_3$) 6.35 (1H, dd), 6.00 (1H, dd), 4.16 (2H, q), 4.00 (2H, s), 3.51 (2H, t), 2.75 (1H, m), 2.4 (1H, m), 2.08 (3H, s), 1.92–1.05 (12H, m), 1.28 (3H, t).

(7) trans-5-(6'-Carboxy-5'-oxahexyl)-6-(1'-[N-phenylthiocarbamoyl)-hydrazono]-ethyl) bicyclo [2,2,2] octane trans-5-(6'-Carboxy-5'-oxahexyl)-6-acetyl-bicyclo [2,2,2]octane (100 mg, 0.35 mmol) in 2 ml dioxan is added to 4-phenylthiosemicarbazide (120 mg, 0.7 mmol) in 20 ml dioxan and the resulting solution is heated for 3 hours at 60° C. The solvent is then removed in vacuo and the residue is purified by liquid-gel partition chromatography using Partisil (10) ODS with acetonitrile/water nitrile/water (70:30 v/v) containing 1% v/v glacial acetic acid run at 3 ml/minute (elution time 5.1 minutes) to give the title compound as a yellow oil (137 mg, 90%), $\lambda_{max}$ (CH$_3$OH) 278 nm, $\delta$(CDCl$_3$) 9.42 (1H, br), 9.34 (1H, br) 8.99 (1H, br), 7.74–7.15 (5H, m), 4.00 (2H, s) 3.48 (2H,t), 1.95 (3H, s), 1.86–1.15 (18H, m).

(B) Preparation of trans-5-(6'-Carboxy-5'-oxahexyl)-6-[1'-(0-diphenylmethoxyimino-methyl)-ethyl]-bicyclo [2,2,2] octane trans-5-(6'-Carboxy-5'-oxahexyl)-6-acetyl-bicyclo [2,2,2] octane (100 mg, 0.35 mmol, prepared as described in Preparation (A) Example 2) in 2 ml dioxan is added to diphenylmethylhydroxylamine hydrochloride (170 mg, 0.7 mmol) in 20 ml of anhydrous pyridine and the mixture is heated for 3 hours at 60° C. The majority of the solvent is then removed and the remaining solution is partitioned between ether and water at pH3–4. The ether layer is dried and evaporated and the resulting residue purified by liquid-gel partition chromatography using Partisil (10) ODS with acetonitrile/water (70:30 v/v) containing 1% glacial acetic acid run at 3 ml/minute (elution time 12.4 minutes) to give the title compound as a colourless oil (113.7 mg, 69%), $\lambda_{max}$ (CH3OH) 258 nm, $\epsilon_{max}$ 5452, $\oplus$(CDCl$_3$) 9.88 (1H, s), 7.28 (1OH, m), 6.19 (1H, s), 4.00 (2H, s), 3.38 (2H, t), 1.87 (3H, s), 1.69–0.95 (18H, m).

(C) Preparation of trans-5-(7'-carboxy-6-oxaheptyl)-6-(1'-[N-(phenylthiocarbamoyl)-hydrazono-ethyl)-bicyclo [2,2,2] octane (1) trans-5-(7'-Carboxy-5'-oxaheptyl)-6-acetyl-bicyclo [2,2,2] octane The procedure of Preparation (A) is followed but commencing with 1,6-hexanediol instead of 1,5-pentanediol and proceeding through ethyl 9-hydroxy-3-oxanonanoate, ethyl 8-formyl-3-oxaoctanoate, ethyl 11-keto-9(E)-3-oxadodecanoate, a mixture of 5-endo-(7'-ethoxycarbon-6'-oxaheptyl)-6-exo-acetyl-bicyclo [2,2,2] oct-2Z-ene and 5-exo-(7'-ethoxycarbonyl-6'-oxaheptyl)-6-exo-acetyl-bicyclo [2,2,2] oct-2Z-ene, and trans-5-(7'-ethoxycarbonyl-6'-oxaheptyl)-6-acetyl-bicyclo [2,2,2] octane to give the title compound as an oil in a similar overall yield,$\nu_{max}$ (film) 1730 (broad), 1705, 1125 cm$^{-1}$, $\delta$(CDCl$_3$) 9.55 (1H, br), 4.08 (2H, s), 3.52 (2H, t), 2.13 (3H, s), 2.15 (1H, m), 1.85 (1H, m), 1.75–1.1 (18H, m).

(2) trans-5-(7'-Carboxy-6'-oxaheptyl)-6-(1'-[N-(phenylthiocarbamoyl)-hydrazano]-ethyl)-bicyclo [2,2,2] octane trans-5-(7'-Carboxy-5'-oxaheptyl)-6-acetyl-bicyclo [2,2,2] octane (100 mg, 0.34 mmol) in 1 ml dioxan is added to 4-phenylthiosemicarbazide (113 mg; 68 mmol) in 20 ml dioxan and the resulting solution is heated for 3 hours at 60° C. The solvent is then removed in vacuo and the residue is purified by liquid-gel partition chromatography using Partisil (10) ODS with acetonitrile/water (70:30 v/v) containing 1% v/v glacial acetic acid run at 3 ml/minute (elution time 17.8 minutes), to give the title compound as a yellow oil (119.7 mg, 80%), $\lambda_{max}$(CH$_3$OH) 287.5 nm, $\epsilon_{max}$ 2580, $\delta$(CDCl$_3$) 9.45 (2H, br), 8.96 (1H, br), 7.08–7.65 (5H, m), 4.00 (2H, s), 3.43 (2H, t), 1.96 (3H, s), 2.25–1.85 (2H, m), 1.8–1.1 (18H, m).

We claim:

1. A method for aiding the regression and palliation of oestrogen-dependent neoplastic disease which comprises administering to a patient in need thereof a therapeutically effective amount of a compound of the formula (I)

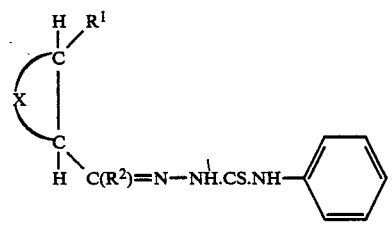

wherein

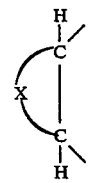

represents one of the divalent cyclic groups

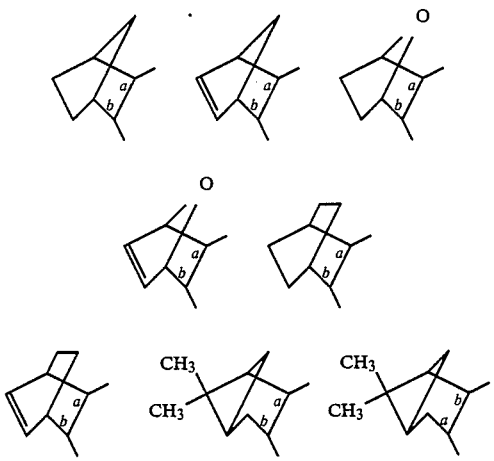

the letters a and b indicating in each case the points of attachment of the substituents $R^1$ and $C(R^2)=N-NH.CS.NH-C_6H_5$, respectively; $R^1$ is a 6-carboxyhex-2-enyl group or a modification thereof in which the group is altered by one, or an appropriate combination of two or more, of the following: (a) alteration of the position of the double bond to the 3,4-position, (b) reduction of the double bond, (c) alteration of the chain length through a decrease or an increase of one methylene group, and (d) formation of a physiologically acceptable amide, ester or salt derivative of the carboxy group; and $R^2$ is hydrogen, methyl or ethyl.

2. A method according to claim 1, in which the divalent cyclic group is a bicyclo [2,2,1] heptane, bicyclo [2,2,1] hept-2Z-ene, bicyclo [2,2,2,] octane or bicyclo [2,2,2,] oct-2Z-ene ring system.

3. A method according to claim 1, in which the divalent cyclic group is a bicyclo [2,2,1] heptane ring system.

4. A method according to claim 1, in which $R^1$ is a 6-carboxyhex-2-enyl group, a 6-carboxyhexyl group or one of such groups in which the chain length is decreased or increased by one methylene group, or a derivative thereof formed at the carboxy group.

5. A method according to claim 1, in which $R^1$ is a 6-carboxyhex-2-enyl group or a derivative thereof formed at the carboxy group.

6. A method according to claim 1, in which $R^2$ is methyl.

7. A method according to claim 1, in which the divalent cyclic group is a bicyclo [2,2,1] heptane or bicyclo [2,2,2] octane ring system, $R^1$ is a 6-carboxyhex-2enyl group and $R^2$ is methyl.

8. A method according to claim 1, in which the configuration about any double bond in the group $R^1$ is cis and in which the substituents $R^1$ and $C(R^2)=N-NH.CS.NH-C_6H_5$ are in a trans relationship.

9. A method according to claim 8, in which any asymetric divalent cyclic group has the 5-endo, 6-exo configuration.

10. A method according to claim 1, in which the compound (I) is 5-endo-(6'-carboxyhex-2'Z-enyl)-6-exo-(1'-[N-(phenylthiocarbamoyl)-hydrazono]-ethyl)-bicyclo [2,2,2] oct-2Z-ene.

11. A method according to claim 1, in which the compound (I) is 5-endo-(6'-carboxyhex-2'Z-enyl)-6-exo-(1'-[N-(phenylthiocarbamoyl)-hydrazono]-ethyl)-bicyclo ]2,2,1] hept-2Z-ene.

12. A method according to claim 1, in which the compound (I) is 5-endo-(6'-carboxyhex-2'Z-enyl)-6-exo-(1'-[N-(phenylthiocarbamoyl)-hydrazono]-ethyl)-bicyclo [2,2,2] octane.

13. A method according to claim 1, in which the compound (I) is 5-endo-(6'-carboxyhex-2'Z-enyl)-6-exo-(1'-[N-(phenylthiocarbamoyl)-hydrazono]-ethyl)-bicyclo [2,2,2] heptane.

14. A method for aiding the regression and palliation of oestrogen-dependent neoplastic disease which comprises administering to a patient in need thereof simulataneously or sequentially amounts which together are therapeutically effective in achieving such regression and palliation of a compound of formula (I) and one or both of an agent for hormonal therapy of neoplasias of oestrogen-dependent tissues and a cytotoxic agent.

15. A method according to claim 14, in which the divalent cyclic group is a bicyclo [2,2,1] heptane ring system, $R^1$ is a 6-carboxyhex-2-enyl group and $R^2$ is methyl.

16. A method according to claim 14, in which the agent for hormonal therapy is tamoxifen.

17. A method according to claim 14, in which the cytotoxic agent is melphalan.

18. A pharmaceutical composition suitable for use in aiding the regression and palliation of oestrogen-dependent neoplastic disease, said composition comprising amounts which together are therapeutically effective in achieving such regression and palliation of a compound of formula (I) as defined in claim 1 and one or both of an agent for hormonal therapy of neoplasias of oestrogen-dependent tissues and a cytotoxic agent together with a physiologically acceptable diluent or carrier.

19. A pharmaceutical composition according to claim 18 in which the divalent cyclic group is a bicyclo [2,2,1] heptane ring system, $R^1$ is a 6-carboxyhex-2-enyl group and $R^2$ is methyl.

20. A pharmaceutical composition according to claim 18, in which the agent for hormonal therapy is tamoxifen.

21. A pharmaceutical composition according to claim 18, in which the cytotoxic agent is melphalan.

* * * * *